United States Patent [19]

McBride

[11] Patent Number: 5,800,721
[45] Date of Patent: Sep. 1, 1998

[54] COMBINED CARDIOTOMY FLUID AND VENOUS BLOOD RESERVOIR

[75] Inventor: Robert R. McBride, Tustin, Calif.

[73] Assignee: Baxter International Inc., Deerfield, Ill.

[21] Appl. No.: 697,814

[22] Filed: Aug. 30, 1996

[51] Int. Cl.$^6$ .......................... B01D 37/00; B01D 35/01
[52] U.S. Cl. ...................... 210/506; 95/242; 96/179; 210/188; 210/436; 210/451; 604/4; 604/122
[58] Field of Search ........................ 210/188, 314, 210/315, 337, 338, 436, 438, 446, 451, 455, 456, 472, 483, 488-490, 492, 645; 604/4, 317, 403, 406, 122; 422/44-48; 95/242; 96/176, 179

[56] References Cited

U.S. PATENT DOCUMENTS

| | | | |
|---|---|---|---|
| 4,026,669 | 5/1977 | Leonard et al. | |
| 4,054,523 | 10/1977 | Ingenito et al. | 210/436 |
| 4,228,125 | 10/1980 | Lobdell et al. | 422/46 |
| 4,424,190 | 1/1984 | Mather, III et al. | 422/46 |
| 4,490,331 | 12/1984 | Steg, Jr. | 422/46 |
| 4,493,692 | 1/1985 | Reed | 604/4 |
| 4,540,399 | 9/1985 | Litzie et al. | 607/4 |
| 4,599,093 | 7/1986 | Steg, Jr. | 55/16 |
| 4,622,032 | 11/1986 | Katsura et al. | 604/122 |
| 4,642,089 | 2/1987 | Zupkas et al. | 604/4 |
| 4,658,655 | 4/1987 | Kanno et al. | 73/863.85 |
| 4,664,682 | 5/1987 | Monzen et al. | 55/178 |
| 4,705,497 | 11/1987 | Shitaokoshi et al. | 604/4 |
| 4,717,377 | 1/1988 | Fukasawa et al. | 604/4 |
| 4,737,139 | 4/1988 | Zupkas et al. | 604/4 |

(List continued on next page.)

FOREIGN PATENT DOCUMENTS

| | | |
|---|---|---|
| 0 122 748 | 3/1984 | European Pat. Off. |
| 0 146 708 | 11/1984 | European Pat. Off. |
| 0 313 107 | 11/1984 | European Pat. Off. |
| 0 207 304 | 2/1986 | European Pat. Off. |
| 0 190 020 A2 | 8/1986 | European Pat. Off. |
| 0 320 815 | 9/1988 | European Pat. Off. |
| 0 401 016 A1 | 12/1990 | European Pat. Off. |
| WO 92/22347 | 12/1992 | WIPO |
| WO93/11808 | 6/1993 | WIPO |
| WO96/00593 | 1/1996 | WIPO |
| WO96/24397 | 8/1996 | WIPO |

OTHER PUBLICATIONS

International Search Report for related PCT Application No. PCT/US97/13485 dated Nov. 28, 1997.
Brochure "HSR–4000 Venas Reservoir with Cardiotemy Antitransfusion Filter", 1993.

*Primary Examiner*—Joseph W. Drodge
*Attorney, Agent, or Firm*—Terry Miller; Debra D. Condino; Guy L. Cumberbatch

[57] ABSTRACT

A combined cardiotomy and venous blood reservoir according to a preferred embodiment of the invention provides a separate in-flow path for both cardiotomy fluid and for venous blood, and includes a cardiotomy fluid filter element also serving as an initial de-foamer. The cardiotomy fluid is de-foamed, filtered, and again de-foamed. The venous blood is de-foamed, and then both fluids are combined for flow from the reservoir. The filter area provided for cardiotomy fluid is advantageously separated from the area of a final de-foamer element. Thus, both the cardiotomy fluid and venous blood may flow through this final de-foamer element simultaneously along separate flow paths. The reservoir design provides greater freedom in selecting adequate filter area for the cardiotomy fluid, while allowing the selection of effective de-foamer element areas in order to achieve acceptable flow rates for both cardiotomy fluid and for venous blood under various conditions of operation for the reservoir. An advantageous ratio of filter and de-foamer element areas to the volume of the reservoir results, with the reservoir requiring only an essential volume of fluid for processing. Also, venous blood and cardiotomy fluid flow inlets to the apparatus may be rotatable in plan view independently both of one another and of a housing of the reservoir.

68 Claims, 4 Drawing Sheets

U.S. PATENT DOCUMENTS

| | | | |
|---|---|---|---|
| 4,743,371 | 5/1988 | Servas et al. | 210/188 |
| 4,765,959 | 8/1988 | Fukasawa et al. | 422/48 |
| 4,846,800 | 7/1989 | Ouriel et al. | 604/4 |
| 5,039,430 | 8/1991 | Corey, Jr. | 210/806 |
| 5,039,482 | 8/1991 | Panzani et al. | 422/46 |
| 5,084,244 | 1/1992 | Muramoto et al. | 422/46 |
| 5,087,250 | 2/1992 | Litchie et al. | 604/321 |
| 5,120,302 | 6/1992 | Vescovini et al. | 604/4 |
| 5,127,900 | 7/1992 | Schickling et al. | 604/4 |
| 5,149,318 | 9/1992 | Lindsay | 604/4 |
| 5,158,533 | 10/1992 | Strauss et al. | 604/4 |
| 5,160,332 | 11/1992 | Nomura | 604/4 |
| 5,186,431 | 2/1993 | Tamari | 251/5 |
| 5,192,439 | 3/1993 | Roth et al. | 210/485 |
| 5,215,450 | 6/1993 | Tamari | 417/474 |
| 5,254,080 | 10/1993 | Lindsay | 604/4 |
| 5,304,164 | 4/1994 | Lindsay | 604/403 |
| 5,305,982 | 4/1994 | Tamari | 251/5 |
| 5,318,510 | 6/1994 | Cathcart | 604/4 |
| 5,336,051 | 8/1994 | Tamari | 417/19 |
| 5,397,299 | 3/1995 | Karwoski et al. | 604/4 |
| 5,399,156 | 3/1995 | Lindsay | 604/4 |
| 5,401,262 | 3/1995 | Karwoski et al. | 604/321 |
| 5,403,273 | 4/1995 | Lindsay | 604/4 |
| 5,403,281 | 4/1995 | O'Neill et al. | 604/113 |

COMBINED CARDIOTOMY FLUID AND VENOUS BLOOD RESERVOIR

BACKGROUND OF THE INVENTION

1. Field of the Invention

The present invention is in the field of reservoirs used during surgery to both recover blood and other body fluid from a surgical site (cardiotomy fluid), and to receive blood from the circulatory system of the patient (venous blood). The recovered cardiotomy fluid and blood are each treated for re-infusion into the patient. For example, the recovered cardiotomy fluid and blood may be subjected to oxygenation, temperature control, and circulatory pumping in a heart/lung apparatus in order to sustain the life of the patient. The cardiotomy fluid recovered from a surgical site additionally requires treatment to remove foreign material that is picked up by exposure to the ambient as well as because of the surgical procedure itself (i.e., tissue particles or bone fragments, as well as ambient bacteria, or particulates from foreign body exposure, for example). Similarly, the venous blood received from the circulatory system must be treated to insure that any entrained bubbles of gas created by extra-corporeal circulation are removed. The collected blood and cardiotomy fluid after treatment are returned to the patient via the heart/lung apparatus.

2. Related Technology

An example of conventional combined cardiotomy and venous blood reservoirs is seen in each of U.S. Pat. Nos. 4,737,139, issued Apr. 12, 1988 to Paul F Zupkas, et al., (the '139 patent); and 5,039,430, issued Aug. 13, 1991 to Edmund R. Corey Jr., (the '430 patent).

The Zupkas '139 patent discloses a cardiotomy and venous blood reservoir. According to the '139 patent the device includes upper and lower chambers which are vertically separated by a horizontal ring-like portion 69 of a support member. This support member ring-like portion 69 serves to divide an upper cardiotomy chamber from a lower venous blood chamber. The cardiotomy fluid which is received by an upper inlet is subjected first to a de-foaming step by a de-foamer 87, then to a filtering step by a depth filter element 89. Finally the fluid is again de-foamed by a de-foamer element 91 which is surrounded by a mesh 93. The venous blood is de-foamed by a lower portion of the de-foamer element, which is shared with the cardiotomy fluid in parallel but fluidly separate flow paths. After flowing radially outwardly through the de-foamer element, both cardiotomy fluid and venous blood flow into a common chamber for return to the patient via a lower outlet of the housing.

With the reservoir taught by the '139 patent, both cardiotomy fluid and venous blood are subjected to a de-foaming step but the cardiotomy de-foamer and the venous blood de-foamer have substantially the same diameter. However, because effective filter area for filtering cardiotomy fluid is a controlling limitation in the design of such reservoirs, the reservoir taught by the '139 patent can be seen to impose a significant limitation on the filter area available for this function. With the device taught by the '139 patent, the effective filter and de-foamer areas in each of the venous blood and cardiotomy fluid flow paths are a function of the fractions of the height of the device which are devoted to each flow path.

Further, it is recognized that the filtering element area provided for cardiotomy fluid must be adequate to pass the necessary fluid volume both at the beginning of use when this filter is clean and unobstructed and entirely available for fluid flow, and also after a period of use as this cardiotomy fluid filter possibly becomes partially clogged by debris. As a result, the ratio of cardiotomy filter area versus volume for the reservoir taught by the '139 patent is or can be unfavorable. The result of this unfavorable ratio can be a reservoir that is limited in cardiotomy filter area, or one which is overly tall in order to achieve an acceptable cardiotomy filter area. Such a tall filter may be overly large and unwieldy for operating room personnel to work with, and may require an excess volume of blood for initial filling.

In other words, because of the common diameters of the filters and de-foamers in these conventional designs, the area available to the cardiotomy filter is simply a function of that part of the height of the device which is devoted to treatment of cardiotomy fluid. Thus, the device either has to be made very tall (with an attendant excessive blood volume and size for the device), or most of the height of the device must be allocated to the cardiotomy flow path. The de-foamer area for the venous blood flow path may be undesirably small as a result.

Viewed another way, the device according to the '139 patent (and similar devices) are seen to provide a branched tributary flow path with one branch receiving cardiotomy fluid and typically effecting a de-foaming, filtering, and de-foaming action on this blood. The other branch of the flow path receives venous blood and effects a de-foaming action only, with the de-foamer being a separate section of the same physical element which effects the final de-foaming of the cardiotomy fluid. The two branches form a confluence, and lead without further blood treatment to the outlet of the device.

The Corey '430 patent effects a separation of filter and de-foamer areas in the cardiotomy flow path as compared to the de-foamer area provided for the venous blood flow path by first filtering and de-foaming the cardiotomy fluid and combining this cardiotomy fluid with venous blood before passing the combined fluid through a final de-foamer element. Thus, it is seen that the blood flow path in this device is branched with a tributary cardiotomy flow path having a filter element and a de-foamer element. The venous blood flow path is a simple tributary entering downstream of the de-foamer in the cardiotomy branch. Downstream of the confluence of the cardiotomy flow path with the venous flow path, the final de-foamer element is situated so that both blood flows pass through this element together.

In view of the above, it can be seen that in order to achieve the most efficient use of space, economy of use of materials of construction, and a desirable ratio of filter and de-foamer areas to reservoir size and volume (while also minimizing the volume of blood required to initially fill a combined cardiotomy and venous blood reservoir), it would be desirable for the filter element of the cardiotomy fluid flow path to also serve a de-foaming function.

Additionally, an improvement could be realized if the final de-foamer element were to be shared between the cardiotomy fluid flow path and the venous blood flow path without imposing the same-area restriction on the design as is seen in the Zupkas '139 device (i.e., with the filter/de-foamer being the same diameter for each flow path with effective areas being a function of the fractions of the height of the device which are devoted to each flow path).

Further, it would be an advantage for purposes of perfusionist convenience and facility in setting up the apparatus if the venous and cardiotomy inlets to such a device were independently rotatable for selection of physical orientation, each with respect to a housing of the device.

SUMMARY OF THE INVENTION

In view of the above, a primary object for this invention is to avoid one or more of the deficiencies of the conventional related technology.

Another objective for this invention is to provide a combined cardiotomy fluid and venous blood reservoir in which a filter element for the cardiotomy fluid flow may also serve a de-foaming function.

Additionally, it is an object for this invention to provide a filter material for use in the cardiotomy flow path which has an additional de-foaming function.

Accordingly, it will be seen that an object for this invention is to provide a cardiotomy flow path in which a filter element is not preceded by a de-foamer element, and in which the filter element itself has a blood de-foaming property.

An additional object for this invention is to provide a combined cardiotomy fluid and venous blood reservoir in which a final de-foamer element may be shared between the cardiotomy fluid flow path and the venous blood flow path without imposing the same-diameter restriction on the design as is seen in the conventional technology (i.e., filter/de-foamer elements of about the same diameter, with effective areas in each flow path dependent upon the fraction of total device height devoted to each flow path).

Yet another object for this invention is to provide a combined cardiotomy and venous blood reservoir which includes a vertically extending partition wall which fluidly separates a surrounding de-foamer element into separate portions, with each portion of the de-foamer element flowing only one of cardiotomy fluid or venous blood.

Another object for this invention is to provide such a combined cardiotomy fluid and venous blood reservoir in which a vertically extending partition wall serves to support a blood-receiving cup within the reservoir.

An object for this invention is to provide such a combined cardiotomy fluid and venous blood reservoir in which a vertically extending partition wall serves to support a tubular member for conveying venous blood vertically downwardly within a chamber of the reservoir, and in which this tubular member is not required to support a blood receiving cup which is disposed at an opening of the tubular member to receive venous blood therefrom and to prevent the reflux of air in the tubular member.

Still further with respect to such a reservoir having a vertically extending partition wall, it is an object for this invention to use this wall to carry a support grate within the de-foamer element, which support grate supports the de-foamer element against radial collapse.

Another object for this invention is to provide such a combined cardiotomy fluid and venous blood reservoir in which the vertically extending partition wall is rotational within a chamber of the reservoir.

Further, an object for this invention is to provide such a combined cardiotomy fluid and venous blood reservoir in which a perfusionist may conveniently set up the apparatus by independent rotation of the venous and cardiotomy inlets in plan view independently of one another. Thus, the perfusionist may select the physical orientation of the blood flow conduits approaching the apparatus for best convenience in view of the position of the patient and the configuration of the surgical suite.

Accordingly, one aspect of the present invention provides a combined cardiotomy fluid and venous blood reservoir having a housing defining a chamber therein and a pair of upper inlets opening into the chamber, one of the pair of upper inlets being a cardiotomy fluid inlet while the other of the pair of inlets is a venous blood inlet; an annular vertically-extending liquid-permeable de-foamer element received in the chamber and having an upper end into which the pair of upper inlets spill; a generally vertically extending partition wall portion received within the de-foamer element between the pair of upper inlets and effectively fluidly dividing the de-foamer element horizontally into a first portion through which flows only cardiotomy fluid, and a second portion through which flows only venous blood; below the de-foamer element the housing defines a basin portion of the chamber for receiving and combining therein of both de-foamed cardiotomy fluid from the first de-foamer element portion and de-foamed venous blood from the second de-foamer element portion; and an outlet leading from the basin portion for flowing de-foamed cardiotomy fluid and de-foamed venous blood out of the housing.

Another facet of the present invention provides a method of treating both cardiotomy fluid and venous blood including steps of flowing the cardiotomy fluid and the venous blood each separately along a respective branch of a branched flow path toward a confluence and an outlet; flowing the cardiotomy fluid through a liquid-permeable filtering element to provide filtered cardiotomy fluid; providing a de-foamer element in both branches of the flow path; de-foaming the filtered cardiotomy fluid and the venous blood by flowing each separately through the de-foamer element; combining filtered and de-foamed cardiotomy fluid and de-foamed venous blood at the confluence of the flow path; and flowing the combined cardiotomy fluid and venous blood together from the outlet.

Still further, the present invention provides a combined cardiotomy fluid and venous blood reservoir having a housing defining a chamber therein and a pair of upper inlets opening into the chamber, one of the pair of upper inlets being a cardiotomy fluid inlet while the other of the pair of inlets is a venous blood inlet; an annular vertically-extending liquid-permeable de-foamer element received in the chamber and having an open upper end into which the pair of upper inlets spill; a vertically extending partition wall portion received within the de-foamer element between the pair of upper inlets and effectively fluidly dividing the de-foamer element horizontally into a first portion through which flows only cardiotomy fluid, and a second portion through which flows only venous blood; a vertically extending tubular member carrying venous blood from the venous blood inlet downwardly into the chamber, the tubular member having an opening to the chamber adjacent to a lower end thereof; and the partition wall carrying a blood-receiving cup adjacent to the lower end of the tubular member, the cup having a rim over which blood received therein flow into the chamber and which is at a higher elevation than the opening, whereby reflux of gaseous fluid upwardly in the tubular member is prevented by a fluid trap formed within the cup by venous blood received therein.

An advantage of the present invention according to a preferred embodiment thereof results from the ability to effect a first de-foaming action on cardiotomy fluid without having to provide a separate first de-foamer element. That is, the cardiotomy fluid filter element according to the preferred embodiment of the invention itself serves as a first de-foamer for the cardiotomy fluid. Further, an effective area for the cardiotomy fluid filter element of the present invention can be selected without being constrained to a diameter for this element selected either for purposes of de-foaming of the cardiotomy fluid, nor to a diameter of this element selected for de-foaming of venous blood. That is, the first cardiotomy filter/de-foamer according to one embodiment of the invention is configured as a bag or sack having effective filtering surface area completely around its perimeter. An alternative embodiment of the invention could provide a separate pre-filter de-foamer for the cardiotomy fluid. If desired, the cardiotomy fluid filter element may be pleated or corrugated to increase its effective filter area. This first filter/de-foamer according to the preferred embodiment of the invention is in fluid flow series with a final de-foamer element, so that fluid flow rates can be matched by selection of effective areas.

Further, the de-foamer for the venous blood flow path may also be dedicated only to this flow path, although the de-foamer element itself may be shared by the two flow paths in the preferred embodiment of the invention. According to the preferred embodiment of the invention, the portion of the de-foamer element dedicated to each one of the two flow paths is selected by the location of a partition wall which in plan view may have an offset to define a trough, and which provides one way of selecting the effective parts of the area of this de-foamer element which are exposed to each of the two flow paths.

Additionally, a better understanding of the present invention will be obtained from reading the following description of a single preferred exemplary embodiment of the present invention when taken in conjunction with the appended drawing Figures, in which the same features (or features analogous in structure or function) are indicated with the same reference numeral throughout the several views. It will be understood that the appended drawing Figures and description here following relate only to one exemplary preferred embodiment of the invention, and as such, are not to be taken as implying a limitation on the invention. That is, no limitation on the invention is implied by this reference, and none is to be inferred.

DETAILED DESCRIPTION OF AN EXEMPLARY PREFERRED EMBODIMENT OF THE INVENTION

Figure 1:
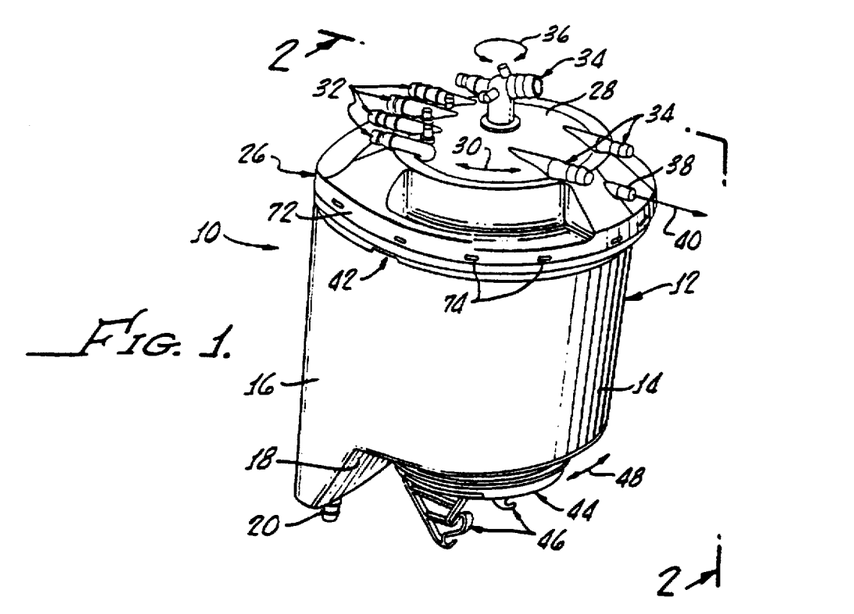
FIG. 1 provides a perspective view of a combined cardiotomy fluid and venous blood reservoir embodying the present invention, and is generally an elevation view of the apparatus.

Viewing FIGS. 1–4 in conjunction with one another, and considering first FIG. 1, a combined cardiotomy fluid and venous blood reservoir 10 is seen in perspective view providing primarily a side elevation view and one-quarter top view. It will be understood that by "cardiotomy fluid" is meant blood and body fluid collected from a patient, usually at a surgical site by means of suction lines, and which cardiotomy fluid is mostly patient blood. This cardiotomy fluid may include other body fluids in addition to blood, is not sterile because of its exposure to the surgical site and ambient air, and may contain tissue particles or bone fragments, for example.

The reservoir 10 includes a housing 12 having a lower portion 14 with a side wall 16 and a lower wall 18 including a fluid outlet 20. The side wall 16 defines an upper edge portion 22 with an upper edge 24 at which an upper portion 26 (or top part) including a rotatable cap or turret assembly (generally indicated with the numeral 28) is sealingly received. As will be seen, the cap part 28 is rotatable relative to the top part 26, as is indicated by arrow 30. Near its outer periphery, cap part 28 carries a plurality of circumferentially arrayed cardiotomy fluid inlets (each referenced generally by the arrowed numeral 32). Inlets 32 are disposed radially or parallel with a radius of cap part 28. At its center, cap part 28 carries a venous blood inlet 34, which is also rotatable relative to the housing 12 and independently of cap part 28, as is indicated by arrowed numeral 36. Opposite to the cardiotomy inlets 32, the turret 28 also carries a pair of parallel venous blood inlets 34'.

The upper portion 26 of housing 12 also includes a connection, indicated with the numeral 38, which may be used as a vacuum connection or as an air vent. Connection 38 provides for fluid flow both inwardly and outwardly of the housing 12. As is indicated by the arrowed numeral 40 on FIG. 1, air flow is predominantly outwardly of connection 38 when a vacuum is applied to this connection. Connections 32, 34, and 38 are of hose-barb configuration to allow convenient connection of the flexible hoses used during a surgical procedure for fluid flow of blood, body fluids, and other fluids, as will be conventionally understood by those ordinarily skilled in the pertinent arts.

Still viewing FIG. 1, it is seen that the housing 12 defines a pair of opposite recesses 42 (only one of which is visible) so that the apparatus can be supported by a stirrup shaped bracket (not shown) extending from a support column (also not shown). The reservoir 10 also includes a lower hanging bracket 44 having a pair of depending hook-shaped portions 46, and which is freely rotatable through an angle of about 20 to 30 degrees, or more, (as is indicated by arrowed numeral 48). The bracket 44 and hooks 46 allow attachment of an oxygenator/heat exchanger to the reservoir 10 for convenient fluid flow interface therewith, while the relative rotational freedom (i.e., arrow 48) of this bracket allows the perfusionist to place and route fluid flow tubing and plumbing most desirably and conveniently.

Figure 2:
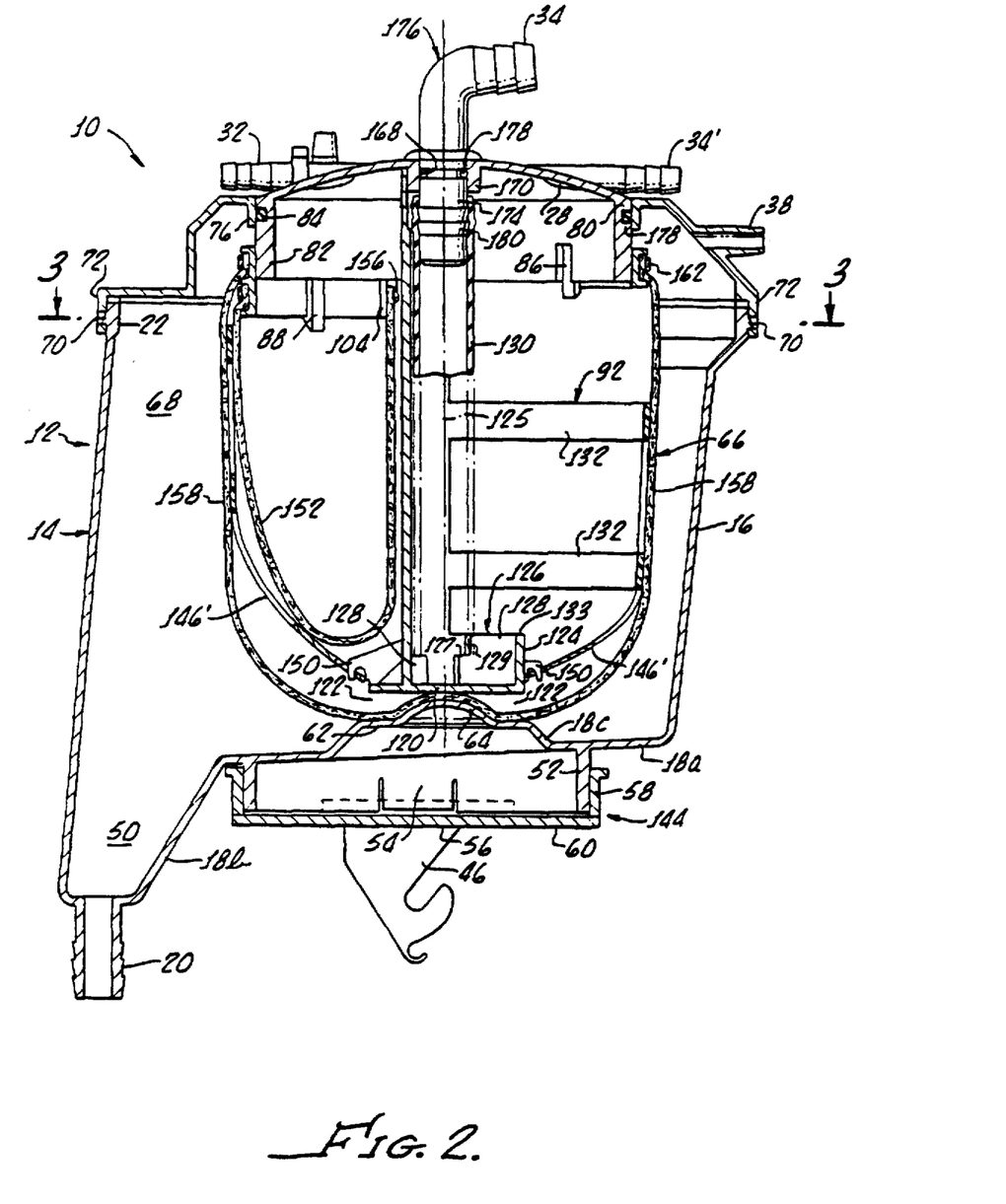
FIG. 2 is a cross sectional elevation view of the apparatus seen in FIG. 1, and is taken at line 2—2 of FIG. 1 looking in the direction of the arrows.
Figure 3:
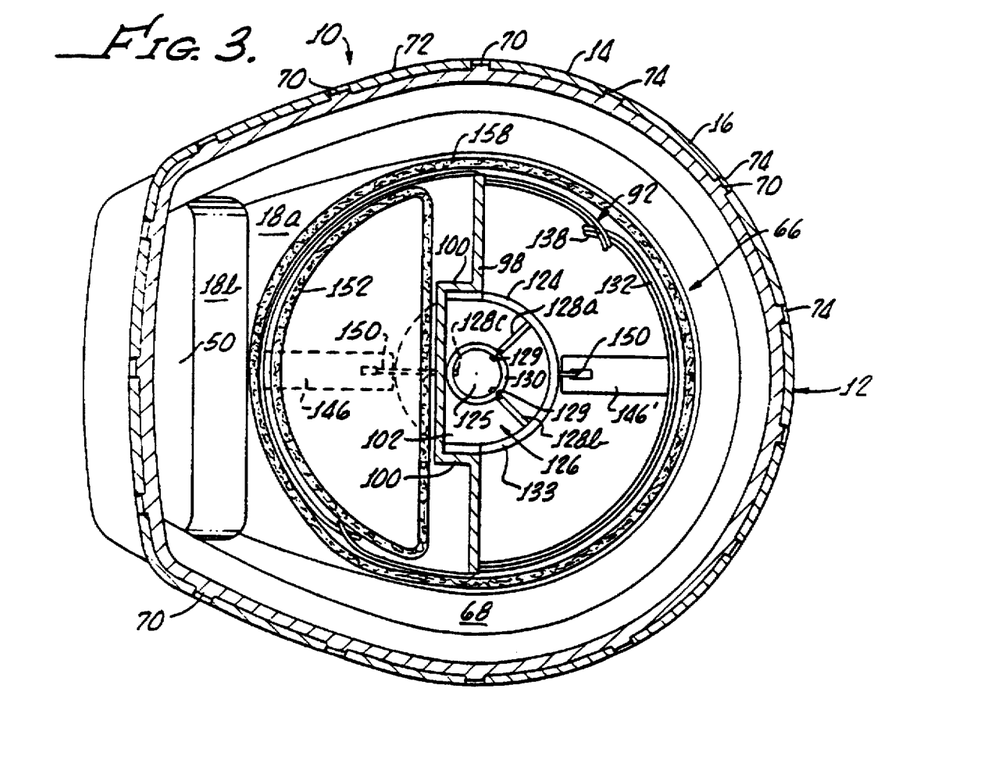
FIG. 3 is a cross sectional plan view taken at line 3—3 of FIG. 2 and looking in the direction of the arrows.
Figures 4, 9:
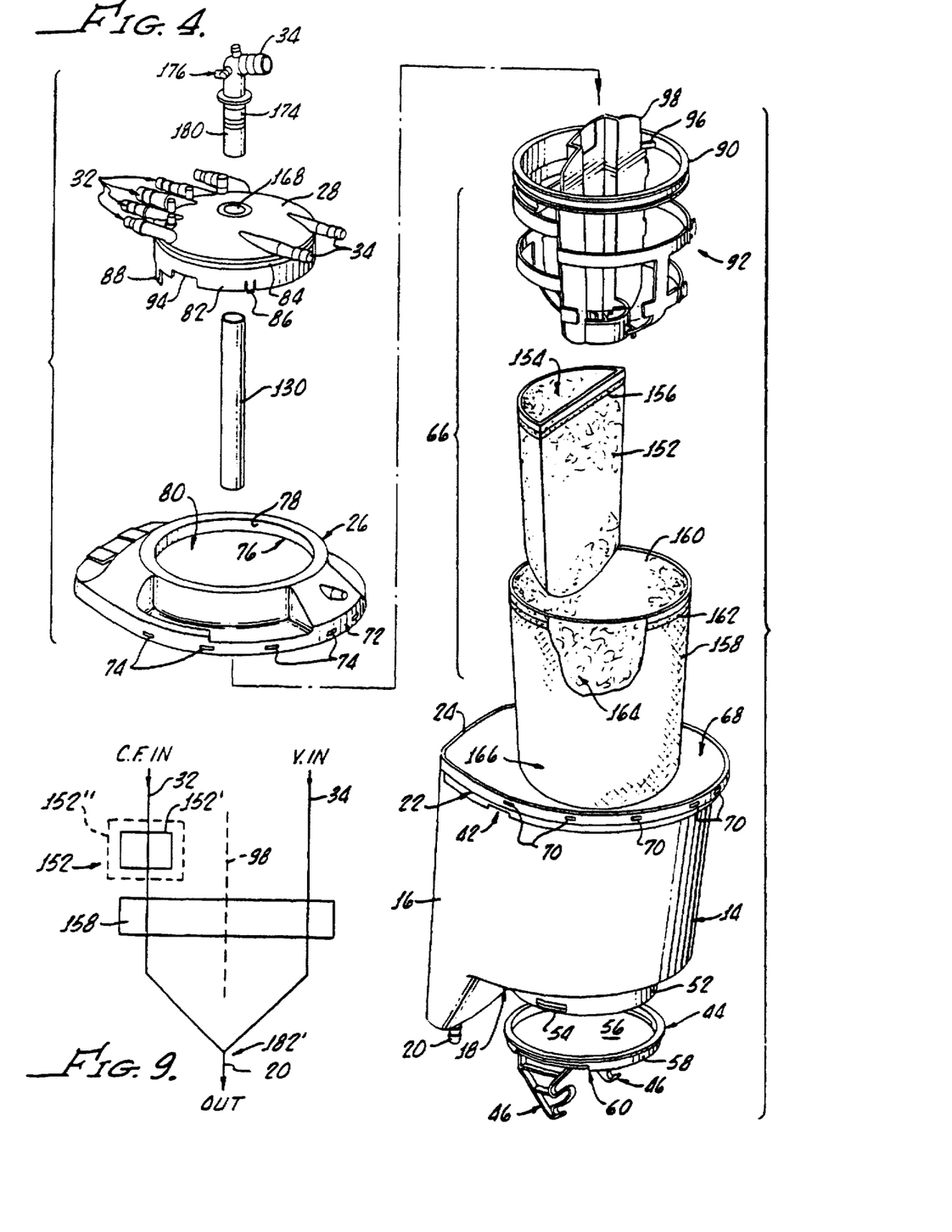
FIG. 4 provides an exploded perspective view of the apparatus seen in FIGS. 1-3, and is taken from a perspective similar to FIG. 1. In this Figure the dash-dot line indicates a continuation of the assembly arrangement (as is indicated by the arrow head on this line), and is used for convenience and economy of laying out the drawing on the sheet.
FIG. 9 provides a schematic of a tributary confluent blood fluid flow circuit provided by the apparatus of the present invention.

Viewing now FIGS. 2–4, and keeping FIG. 1 in view as well, it is seen that the lower wall 18 of lower housing portion 14 includes both a gently sloped wall part 18a, and a more steeply sloped wall part 18b leading into a basin 50.

The basin 50 communicates outwardly of the reservoir 10 via outlet 20, which is also of hose-barb configuration. From the wall portion 18a depends a circular lip 52 having a diametrically opposite pair of resilient pawl-fingers 54. Carried on this circular lip 52 by the fingers 54 is the bracket 44, which includes a circular central wall portion 56 carrying the hooks 46 and being carried by a circular upwardly extending peripheral wall portion 58. This peripheral wall portion 58 circumscribes the lip 52 and defines a pair of opposite outwardly opening slots 60 in which the fingers 54 are movably received to allow about 20 to 30 degrees of rotational freedom for the bracket 44, recalling arrow 48.

Centrally of the portion 18a (viewing FIG. 2), the lower wall 18 defines an upwardly protruding portion 18c, which leads to a plateau 62 where a crown or arcuate upward protrusion 64 of the wall portion 18 is disposed. As will be seen, a support, filter, and de-foamer assembly (generally indicated with the numeral 66) is rotatably seated upon the crown 64. As is best seen in FIG. 2, this support/filter assembly 66 is disposed within a chamber 68 cooperatively defined by the lower portion 14, upper portion 26, and cap part 28 of the reservoir 10.

Still viewing FIG. 2, and keeping FIGS. 1 and 4 at hand, it is seen that the upper edge portion 22 of the lower portion 14 is rather thickened, and defines a plurality of outwardly extending fingers 70. The top part 26 includes a depending lip portion 72 which circumscribes the portion 22 of the lower portion 14, and which defines a plurality of outwardly opening apertures 74. The fingers 70 are received into the apertures 74 so that the upper portion 26 is retained on the lower portion 14. A sealing relation may be maintained between the upper portion 26 and lower portion 14 either by inclusion therebetween of a gasket material (not shown) or by use of a sealing material between these components. Thus, it will be appreciated that a vacuum communicated into chamber 68 via port 38 may be effective to maintain this chamber at a sub-ambient pressure, and to cause the collection of cardiotomy fluid and body fluids via the ports 32 and suction lines (not shown) attached thereto during or after a surgical procedure. Ordinarily, during a surgical procedure, the chamber 68 will be at a lower level than the patient, so that venous blood flows into the chamber by gravity and a vacuum is not necessary to draw this blood into the reservoir 10.

As is best seen in FIG. 4, the upper portion (i.e., top) 26 includes a depending wall part 76 having a radially inwardly disposed surface 78 and defining a circular opening 80. The turret 28 is rotationally received in opening 80, and includes a depending lip 82 which outwardly carries an O-ring type of sealing member 84. The O-ring 84 engages surface 78 to sealingly separate the chamber 68 from ambient while still allowing relative rotation of turret 28. The lip 82 of turret 28 includes two adjacent comparatively shorter pawl fingers 86 (only one of which is seen in the drawing Figures), and two adjacent comparatively longer pawl fingers 88 (also only one of which is seen in the drawing Figures) which are each diametrically opposite to the fingers 86. As is best seen in FIG. 2, and which can be appreciated also by viewing FIG. 4, the fingers 86 and 88 engage an upper ring portion 90 of a support member 92 forming a part of the support/filter and de-foaming assembly 66, as will be further explained.

In order to complete this description of the turret member 28 and its cooperation with the support/filter and de-foamer assembly 66, it will be noted as is seen best in FIG. 4, that the depending lip 82 defines a pair of notches 94 (only one of which is visible in FIG. 4) which at their side edges engage respective buttresses 96 defined inwardly of the ring portion 90 at its junction with a transverse wall 98 extending diametrically from side to side within the ring portion 90 of support member 92. Accordingly, the support/filter and de-foaming assembly 66 is rotationally coupled to the turret member 28 so that as this turret is rotated to align ports 32, the filter/de-foamer assembly 66 rotates within housing 12 and chamber 68.

Figure 5:
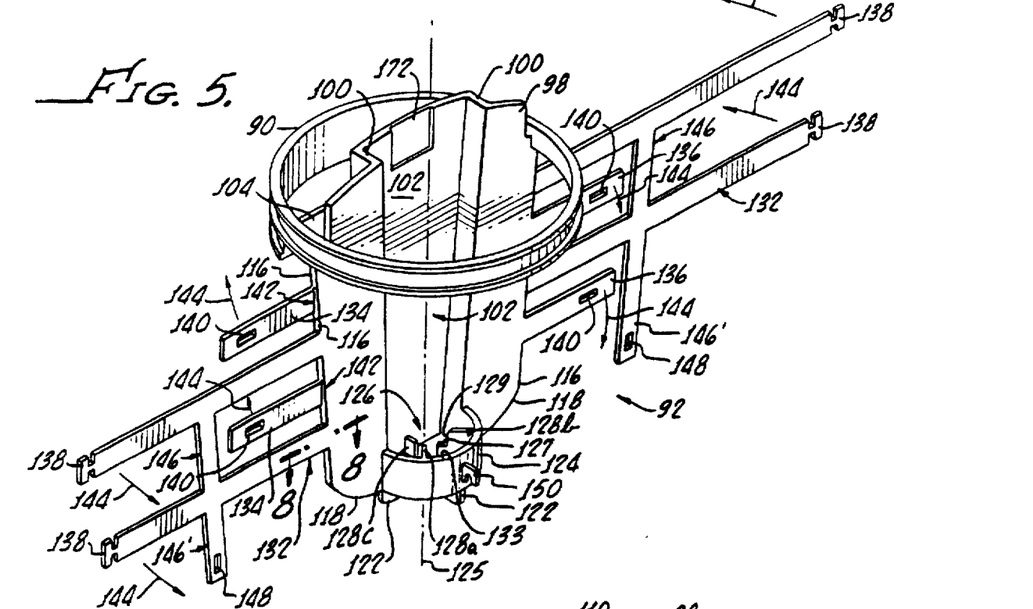
FIGS. 5 and 6 are perspective views of a component part of the apparatus, and are shown in a pre-assembly configuration and in a use configuration, respectively, in order to better illustrate features of the structure.

Viewing FIGS. 5 and 6, it is seen that the support member 92 is preferably formed as a plastic molding having integral features as described above, and as are further described below. FIG. 5 illustrates the pre-assembly configuration of this plastic molding. Viewing FIG. 5, it is seen that the support member 92 includes both the transverse wall portion 98, which is offset at parts 100 to define a vertically extending centrally located trough 102, but also includes a vertically extending short wall portion 104 extending from side to side parallel to but spaced slightly from wall portion 98. The ring member 90 is of two differing depths in the vertical direction, with the demarkation between these depths being marked by the juncture of wall portion 104 with the ring portion 90. Stated differently, the wall portion 104 defines a circular segment of the ring member 90 and cooperates therewith to define a D-shaped depending portion of this ring member.

It further will be noted that the depth of the trough 102 in the horizontal sense (i.e., the distance of the offset in wall 98) effects the areas of the final de-foamer element which will be exposed to cardiotomy fluid and venous fluid flows, respectively. In the preferred embodiment illustrated, the offset of wall 98 is such that one-half of the final de-foamer element is exposed to each flow path. However, this need not be the case, and the offset can be selected to favor either flow path with a larger portion of the final de-foamer element area according to the wishes of the designer, as will be seen.

Figures 6, 7, 8:
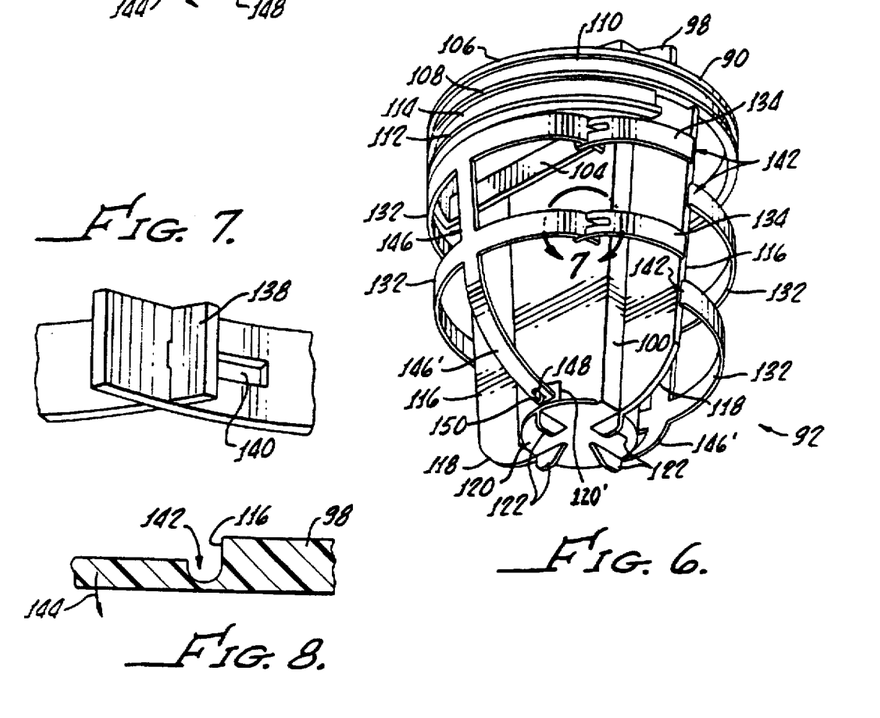
FIG. 7 is an enlarged perspective view of an indicated encircled portion of FIG. 6, and is seen from the side opposite to that seen in FIG. 6 (i.e., from an inner perspective looking radially outwardly generally toward the viewer of FIG. 6)
FIG. 8 is an enlarged cross sectional view taken at line 8—8 of FIG. 5 looking in the direction of the arrows.

Considered from the top downwardly, with reference to FIG. 6, the ring portion 90 includes a pair of vertically spaced apart radially outwardly extending ridges 106 and 108 which cooperatively define a circumferentially continuous groove 110 circumscribing the ring portion 90. Below the ridge 108 is a second ridge 112 extending only about the vertically deeper portion of ring portion 90 (i.e., terminating at wall 104), and cooperating with the ridge 108 to define a groove 114 extending about half way about the ring portion 90. It will be noted in FIGS. 4, 5, and 6, that line of sight communication between the terminations of groove 114 can be had along the short wall portion 104. The significance of this feature will be explained below.

Further considering FIGS. 5 and 6, it is seen that below the ring portion 90, the wall portion 98 of support member 92 includes opposite side edges 116 leading downwardly to an arcuate lower edge 118. Centrally of the lower edge 118 is disposed a horizontally extending plate-like portion 120 of the support member 92, which on its lower side (seen in FIG. 6) carries four circumferentially arrayed and diametrically opposed depending flange features 122. These flange features 122 straddle the crown 64 (indirectly, because other structure is interposed) to effectively locate the lower end of the support/filter and de-foaming assembly 66 in the housing 12 while allowing relative rotation of this assembly 66.

As is seen best in FIG. 5, on the side of wall portion 98 having the trough feature 102, a peripheral wall portion 124 extends upwardly from the plate-like portion 120 to define an upwardly opening blood-receiving cup 126. Inwardly of this cup 126, three convergent flanges (each generally referenced with numeral 128) extend toward but short of intersection with one another at the rotational axis (indicated with numeral 125 on FIG. 5) of the support/filter and de-foaming assembly 66. The two of these flanges 128 (indicated as 128a and 128b) which are spaced from wall portion 98 are stepped to each define both a horizontally extending support edge 127 and a vertically extending locating edge 129 for a central venous-blood inflow tube 130 (best seen in FIGS. 2, 3, and 5). This venous blood inflow tube 130 is supported primarily from above by structure to be described below. However, it should be appreciated that the partition wall 98 may serve a support and locating function with respect to the tube 130. The third flange feature 128c extends from wall portion 98 into the cup 126 and simply provides a support edge 127 for the tube 130 (the tube 130 being trapped between edges 129 and wall 98). Thus, it will be seen that the lower extent of the tube 130 is trapped in alignment with cup 126 between the wall 98 and the locating edges 129, with a lower opening 131 of this tube within cup 126 and below an upper edge 133 of wall 124. Thus, it is seen that the cup 126 is entirely supported by the partition wall 98.

Still viewing FIGS. 5 and 6, it is seen that the support member 92 includes a pair of opposite, somewhat H-shaped, grate structures 132 extending laterally from each one of the side edges 116. The grate structures 132 are offset from one another vertically. Interdigitated with the grate structures 132 (in the pre-assembly configuration shown in FIG. 5) are opposite pairs of grate arms 134 and 136, which are also offset from one another vertically, but which align with the grate structure 132 on the opposite side of the wall portion 98. The outer end portions of each structure 132 are provided with T-shaped tabs 138, while the outer ends of the arms 134 and 136 are provided with slots 140 (see, FIG. 7). Also, as is seen in FIG. 8, at the juncture of each structure 132, and of each arm 134 and 136, with wall structure 98 (i.e., at the side edges 116), a notch 142 is provided to define an integral living hinge portion (indicated with the numeral 142'). The positions of the notches 142 are arranged so that the structures 132 and arms 134, 136 have a preferred bending direction, as is indicated on FIGS. 5 and 8 with arrows 144.

Accordingly, the structures 132, and arms 134, and 136 may be folded perpendicularly to the wall portion 98 at their points of attachment thereto (i.e., at hinge features 142') to bend circumferentially around, and to be interconnected at the tabs 138 and slots 140, as is best illustrated in FIG. 7. This places the grate structure generally in the use configuration seen in FIG. 6. However, it will be noted that the grate structures 132 also include vertically extending grate bar 146 which have a lower portion 146 ' provided with a vertically extending slot 148. A vertical web 120' above the plate-like portion 120, and the wall 124 of cup 126, are each provided with a respective hook feature 150 onto which the portions 146' are hooked at slots 150. Consequently, the support structure 92 is thus converted from its pre-assembly configuration of FIG. 5 to a use configuration, as seen in FIGS. 2, 3, 4, and 6. In this use configuration, the grate structure (132, 134, 136 with vertical bar parts 146) supports a de-foamer element against radial collapse, as will be seen.

As is seen in FIGS. 2 and 4, on the side of support structure seen in FIG. 6, a bag 152 of depth filter material is secured at its open upper end 154 to the ring portion 90 and wall 104 by a tie strap 156 received about this bag 152 and into the groove 114. This tie strap 156 and a portion of the bag 152 adjacent to the open upper end 154 extend across wall 104 between the terminations of the groove 114, as was alluded to above. It will be appreciated that because the bag 152 is within the grate structure described above, this bag is placed into position and secured with strap 156 before the grate structure is completed into the configuration seen in FIG. 6. As will be explained below, the bag 152 also functions as a first cardiotomy fluid de-foamer element. That is, the depth filter bag 152 is fabricated of a depth filter element material which has preferably been treated according to the teachings of this invention in order to render it effective also as a first de-foamer element acting on cardiotomy fluid and blood received into the bag 152, as will be explained below.

After placement and securing of the bag 152, and completion of the grate structure to the configuration seen in FIG. 6, a two-part de-foamer bag structure 158 is placed about the support structure 92 (i.e., around the grate structure previously described). At its open upper end 160, the bag structure 158 is secured to ring portion 90 by a tie strap 162 received in groove 110. The bag structure 158 at its closed lower extent is received slidably (i.e., rotationally) on the crown 64 and is conformal to this crown to allow the flanges 122 to effect rotational positioning of the support/filter and de-foaming structure 66 at its lower end as was mentioned above. The de-foamer bag structure 158 is formed of an inner bag 164 of open-cell reticulated polyurethane material, and an outer bag 166 of mesh fabric material. As is known, the polyurethane material is treated with a silicone or other effective de-foaming agent.

It will be noted that the de-foamer bag structure 158 is also snug to vertical wall portion 98 from top to bottom so that this wall portion 98 effectively divides the de-foaming materials (i.e., inner and out bag members 164, and 166) of the outer de-foaming bag structure 158 horizontally into two separate portions so far as fluid flow from within this bag structure outwardly is concerned. That is, the portion of de-foamer bag structure 158 which is disposed on the side of support structure 92 seen predominantly in FIG. 5 will effect the final de-foaming of venous blood only. This is the singular de-foaming step performed on the venous blood. Conversely, the portion of the de-foamer bag structure 158 which is disposed on the side of support structure 92 seen predominantly in FIG. 6 will effect the final de-foaming of cardiotomy fluid. Importantly, it should be noted that the cardiotomy fluid will have been filtered and effectively de-foamed by the bag structure 152 before flowing to de-foamer 158. FIG. 9 will be discussed below to further explain the fluid flow path circuit effected by the reservoir 10.

Returning now to a reconsideration of FIG. 4, it is seen that the turret 28 defines a central opening 168 circumscribed by a downwardly extending wall 170, best seen in FIG. 2. The wall portion 98 includes a thinned or recessed part 172 as is seen in FIG. 5 to clear both the lower end of this wall 172 and the upper end of the tube 130, as will be seen. Rotationally received in the opening 168 is a stem portion 174 of a fitting 176. This fitting 176 defines the venous blood inlet 34, and carries an O-ring type of sealing member 178. The O-ring sealing member 178 engages the surface of wall portion 170 to allow relative rotation of fitting 176 independently of rotation of turret member 28, and independently of the housing 12.

Because the tube member 130 is relatively rotationally guided at its lower end in the cup 126 by flanges 128, the support/filter and de-foaming assembly 66, and venous blood fitting 176 are each fully rotational in plan view independently of housing 12 and independently of one another. While rotation of the turret member 28 will carry fitting 176 in rotation as well, manual constraint or rotation of fitting 176 to a selected rotational position is easily effected.

Inwardly of the housing 12 (that is, in chamber 68), the fitting 176 defines a portion 180 on which the upper end of tube 130 is received. As is best seen in FIG. 2, the lower end of tube 130 is supported on the steps 127 of the stepped flanges 128 to be supported above the floor of cup 126 (that is, above the upper surface of plate-like portion 120, and at an elevation below the top edge 133 of peripheral wall portion 124). The tube 130 at its lower end is also generally centered on the crown feature 64 in plan view. Consequently, a liquid trap feature is formed which prevents the reflux of air or other gas upwardly into the open lower end of tube 130. As a result, during use of the reservoir 10 the tube 130 normally runs full of venous blood and both splashing of the blood as well as the possibility of the occurrence of an air embolism from air reflux into the circulatory system are prevented.

Having observed the structure of the combined cardiotomy and venous blood reservoir 10 as described above, its operation and use in a surgical procedure will be apparent to those ordinarily skilled in the pertinent arts. However, consideration now of FIG. 9 will assist the reader in understanding how the dual-function of filter-de-foamer material 152 is realized and utilized in the preferred embodiment of the invention. In FIG. 9 it is seen that a branched flow path 182 extends from inlets 32 and 34 to outlet 20. At the inlet 32, the notation, "C.F. IN", means that cardiotomy fluid is received at this inlet. Similarly, at inlet 34, the notation, "V. IN", means the venous blood is received. The flow path 182 is confluent, so that the path from inlet 32 and the path from inlet 34 are tributaries to the flow from outlet 20. Now, it is seen that in the preferred embodiment of the invention the flow received in inlet 32 is first exposed to depth filter material 152 which appears to include a filter element (indicated on FIG. 9 with numeral 152'), but which also includes an effective de-foaming action (indicated with numeral 152" on FIG. 9). Consequently, the cardiotomy fluid is effectively de-foamed and filtered simultaneously. Fluid in the cardiotomy branch next flows to and through a respective portion of the de-foamer element 158 (that is, on the respective side of the wall portion 98), and is subjected to another de-foaming step. Similarly, on the venous blood side of the flow path 182, the blood is de-foamed by a respective part of de-foamer element 158. Next, the flow paths form a juncture at 182', and the de-foamed fluid from both branches flows from outlet 20.

It will be recognized that instead of using a combined filter/de-foamer element 152, it is possible within the ambit of the present invention to provide a separate de-foamer element for cardiotomy fluid upstream of filter element 152. In this case, the filter element 152 would not need to be treated to act also as a de-foamer itself. The de-foamer element upstream of filter 152 could simply be configured as another bag of de-foamer material like that used for de-foamer 164. An additional modification of the reservoir 10 would include the inclusion of separate bags of elements of de-foamer material for each of the cardiotomy fluid branch and for the venous blood branch of the branched flow path illustrated by FIG. 9. In such an alternative construction, the separation indicated by dashed line 98 in FIG. 9 would be an actual separation because two separate elements of de-foamer material would be used. This construction would allow a further freedom of selection of relative areas for the cardiotomy de-foamer element versus the venous blood de-foamer element. Still additionally, a modification to the reservoir disclosed and described above could be effected by pleating or corrugating the filter element 152. The use of pleated or corrugated filter elements is known in the art, and has the advantage of allowing a further increase in effective filter area for the cardiotomy fluid flow path without increasing the outward physical size of the reservoir 10.

In order to realize the benefit of not having to provide a separate cardiotomy fluid de-foamer element upstream of filter 152 (as was conventional in the art heretofore), and of also realizing concurrent de-foaming and filtering of cardiotomy fluid at a first filter element, the present invention provides a filter material which preferably is a depth filter material, and which also preferably is itself treated with an active defoaming agent. That is, depth filter material suitable for use with human blood and body fluids is subjected to a treatment to activate its surface as a de-foaming surface as well. In other words, one method of achieving this end is to immerse a depth filter material in a bath of liquid carrier, such as a freon, which has a de-foaming agent, such as a suspension of silicone or a silicate material, therein. The filter material upon withdrawal from the liquid bath and dried of the carrier will retain sufficient quantity of the active de-foamer agent to be effective as a first de-foamer for cardiotomy fluid in the flow path 182, while also being effective still as a filtering agent for this liquid. An example of this defoaming material is known in the art as "Tween 80", and is a surfactant. Heparin may also be added as a coating on the material, which will inhibit clotting of blood and resultant clogging of the filter 152.

Upon further consideration of the apparatus herein depicted and described, it will be apparent that a combined cardiotomy fluid and venous blood reservoir with a fluid flow chamber which is horizontally divided into two parallel and separate flow paths by a vertically extending partition wall (i.e., the wall portion 98) is provided. The final de-foamer material 158 is thus effectively divided into separate portions for respectively treating cardiotomy fluid and venous fluid, while the surface area of the filter bag 152 for cardiotomy fluid is not necessarily limited by a "same diameter" design (i.e., substantially to an area constrained to be about the "same" as a portion of the venous blood final de-foamer), as are some prior designs. This is the case because the filter/de-foamer 152 may be made of a size sufficient to filter and de-foam the cardiotomy fluid over all of its surface area while only utilizing a sector (in plan view) of the final de-foamer. On the other hand, the area of the final de-foamer element 154 can be made as large as necessary while still controlling volume (and blood capacity) of the apparatus by selecting its diameter and vertical depth beyond that of the first filter/de-foamer bag 152. Accordingly, an uncommon flexibility is provided by the present invention in selecting the relative sizes, areas, and fluid flow capacities of the elements of the apparatus (i.e., filters and de-foamers) while still realizing an apparatus of desirably small size and without excessive blood capacity. Further, the present invention provides a combined cardiotomy fluid and venous blood reservoir in which the fluid flow connections for cardiotomy fluid may be rotationally positioned in plan view independently of the housing of the device. Also, the fluid flow connection for venous blood receipt into the device may be positioned rotationally in plan view independently of the housing. Both cardiotomy and venous blood connections may be rotationally positioned independently of one another in plan view. Thus, the perfusionist using a device according to the present invention has an uncommon freedom of routing and connection possibilities for the cardiotomy and venous blood flow conduits used during a surgery or other procedure.

While the present invention has been depicted, described, and is defined by reference to a single particularly preferred embodiment of the invention, such reference does not imply a limitation on the invention, and no such limitation is to be inferred. The invention is capable of considerable modification, alteration, and equivalents in form and function, as will occur to those ordinarily skilled in the pertinent arts. The depicted and described preferred embodiment of the invention is exemplary only, and is not exhaustive of the scope of the invention. Consequently, the invention is intended to be limited only by the spirit and scope of the appended claims, giving full cognizance to equivalents in all respects.

I claim:

1. A combined cardiotomy fluid and venous blood reservoir comprising:

a housing defining a chamber therein and a pair of upper inlets opening into said chamber, one of said pair of upper inlets being a cardiotomy fluid inlet while the other of said pair of inlets is a venous blood inlet;

an annular vertically-extending liquid-permeable de-foamer element received in said chamber and having an upper end into which said pair of upper inlets spill;

a generally vertically extending partition wall portion received within said de-foamer element between said pair of upper inlets and effectively fluidly dividing said de-foamer element horizontally into a first portion through which flows only cardiotomy fluid, and a second portion at approximately the same elevation as said first portion through which flows only venous blood;

a basin portion of said housing chamber defined below said de-foamer element for receiving both de-foamed cardiotomy fluid and de-foamed venous blood from said second de-foamer element portion; and an outlet leading from said basin portion for flowing de-foamed cardiotomy fluid and de-foamed venous blood out of said housing.

2. The combined cardiotomy fluid and venous blood reservoir of claim 1 further including a primary cardiotomy fluid filter configured as a bag member having an open upper end, said primary cardiotomy fluid filter being disposed within said chamber within said de-foamer element and below said cardiotomy fluid inlet to received cardiotomy fluid therefrom.

3. The combined cardiotomy fluid and venous blood reservoir of claim 1 further including a support member rotationally received within said chamber, said support member defining said partition wall portion and also including a retaining portion adjacent an upper extent of said partition wall portion; and a primary cardiotomy fluid filter disposed upon said retaining portion of said support member within said chamber and below said cardiotomy fluid inlet within said de-foamer element.

4. The combined cardiotomy fluid and venous blood reservoir of claim 3 wherein said retaining portion includes a depending wall portion including a circumferentially extending part of said retaining portion and a transverse wall portion thereof forming a segment of said retaining portion, said primary cardiotomy fluid filter being configured as a bag member having an open upper end, and said bag member at said open upper end being received upon said depending wall portion, and means for securing said bag member upon said retaining portion.

5. The combined cardiotomy fluid and venous blood reservoir of claim 4 wherein said retaining portion includes a circular ring portion and said depending wall portion cooperates with said ring portion to cooperatively define a portion thereof which is generally D-shaped in plan view.

6. The combined cardiotomy fluid and venous blood reservoir of claim 5 wherein said de-foamer element is also configured as a bag-shaped member having a circular open upper end, said bag-shaped de-foamer element at said circular open upper end being received about said ring portion, and means for securing said bag-shaped de-foamer element upon said ring portion.

7. The combined cardiotomy fluid and venous blood reservoir apparatus of claim 6 wherein said means for securing said bag-shaped de-foamer element upon said ring portion includes an elongate securing member circumscribing both said bag-shaped de-foamer element at an upper edge portion thereof and said ring portion.

8. The combined cardiotomy fluid and venous blood reservoir apparatus of claim 7 wherein said elongate securing member includes a tie strap.

9. The combined cardiotomy fluid and venous blood reservoir of claim 4 wherein said means for securing said primary cardiotomy fluid filter bag member upon said retaining portion includes a securing member circumscribing both said bag member at an upper edge portion thereof and a part of said retaining portion at said D-shaped depending wall portion thereof.

10. The combined cardiotomy fluid and venous blood reservoir of claim 9 wherein said securing member includes a tie strap.

11. The combined cardiotomy fluid and venous blood reservoir apparatus of claim 9 wherein said ring portion includes a pair of radially outwardly extending circumferential ridges defining an upper circumferentially continuous groove on said ring portion, and said tie strap for said bag-shaped de-foamer element is received in said upper groove, a lower one of said pair of ridges cooperating with a radially outwardly extending ridge circumscribing only said D-shaped wall portion to define a lower second groove on said ring portion, and said tie strap for said primary cardiotomy fluid filter bag being received into said lower second groove.

12. The combined cardiotomy fluid and venous blood reservoir of claim 3 wherein said support member further includes a support grate extending circumferentially from opposite side edges of said vertically extending partition wall portion, said support grate supporting said de-foamer element against radial collapse.

13. The combined cardiotomy fluid and venous blood reservoir of claim 1 wherein said housing includes a top part defining an upwardly opening aperture which is circular in plan view and which is disposed over said chamber; a turret member which is circular in plan view being rotationally and sealingly received in said circular opening of said top part and defining the one of said pair of inlets which is said cardiotomy fluid inlet; said turret member defining a centrally located aperture; and a venous blood inlet fitting sealingly and rotationally received in said centrally located aperture and defining the other of said pair of upper inlets.

14. The combined cardiotomy fluid and venous blood reservoir of claim 13 further including a support member rotationally received within said chamber, said support member defining said partition wall portion, wherein said turret member and said support member define cooperating means for drivingly coupling said turret with said support member so that manual rotation of said turret member rotates said support member in unison therewith.

15. The combined cardiotomy fluid and venous blood reservoir of claim 13 wherein said venous blood fitting carries a vertically extending tubular member carrying venous blood from said venous blood inlet downwardly into said chamber, said tubular member having an opening to said chamber adjacent to a lower end thereof, and said partition wall portion carrying a blood-receiving cup adjacent to said lower end of said tubular member and receiving said lower end of said tubular member.

16. The combined cardiotomy fluid and venous blood reservoir of claim 15 wherein said blood-receiving cup supports a lower portion of said tubular member.

17. The combined cardiotomy fluid and venous blood reservoir of claim 16 wherein said blood-receiving cup includes a radially extending flange having a horizontally extending surface portion engageable by said lower end of said tubular member to support the latter.

18. The combined cardiotomy fluid and venous blood reservoir of claim 17 wherein said radially extending flange of said blood-receiving cup includes a step defining said a horizontally extending surface portion and also providing a vertically extending surface portion engageable by said tubular member to constrain said tubular member within said cup.

19. The combined cardiotomy fluid and venous blood reservoir of claim 15 wherein said blood-receiving cup includes a peripheral wall portion cooperating with said partition wall and having an upper edge at a higher elevation than said opening of said tubular member.

20. The combined cardiotomy fluid and venous blood reservoir of claim 15 wherein said blood-receiving cup also includes at least two convergent flanges extending toward but short of intersection with one another and being stepped to each define both a horizontally extending support edge confronting said lower end of said tubular member and a vertically extending locating edge engageable with an outer surface of said tubular member to position the latter within said blood-receiving cup.

21. A method of treating both cardiotomy fluid and venous blood, said method comprising steps of:
    flowing said cardiotomy fluid and said venous blood each separately into a reservoir through at least two inlets at an upper end thereof, and out of the reservoir through a common outlet formed therein by
    separating the cardiotomy and venous blood flows about a generally vertical plane to define two side-by-side flow branches upstream of said common outlet;
    flowing said cardiotomy fluid through a liquid-permeable filtering element to provide filtered cardiotomy fluid;
    providing at least one de-foamer element between the two inlets and the outlet;
    de-foaming said filtered cardiotomy fluid and said venous blood by flowing each separately and at approximately the same elevation through said at least one de-foamer element;
    combining filtered and de-foamed cardiotomy fluid and de-foamed venous blood after said defoaming step; and
    flowing said combined cardiotomy fluid and venous blood together from said outlet.

22. The method of claim 21 further including the step of using said liquid-permeable filtering element also to de-foam said cardiotomy fluid.

23. The method of claim 21 wherein the defoaming step includes using a single de-foamer element to de-foam both said cardiotomy fluid and said venous blood.

24. The method of claim 23 further including the step of providing a partition wall fluidly dividing said single de-foamer element into a first portion through which flows only cardiotomy fluid and a second portion through which flows only venous blood.

25. A combined cardiotomy fluid and venous blood reservoir comprising:
    a housing defining a chamber therein and a pair of upper inlets opening into said chamber, one of said pair of upper inlets being a cardiotomy fluid inlet while the other of said pair of inlets is a venous blood inlet;
    an annular vertically-extending liquid-permeable de-foamer element received in said chamber and having an open upper end into which said pair of upper inlets spill;
    a vertically extending partition wall portion received within said de-foamer element between said pair of upper inlets and effectively fluidly dividing said de-foamer element horizontally into a first portion through which flows only cardiotomy fluid, and a second portion through which flows only venous blood;
    a vertically extending tubular member in said second portion carrying venous blood from said venous blood inlet downwardly into said chamber, said tubular member having an opening to said chamber adjacent to a lower end thereof; and
    said partition wall carrying a blood-receiving cup extending into said second portion and receiving said lower end of said tubular member, said cup having a rim over which blood received therein flows into said second portion and which is at a higher elevation than said opening, whereby reflux of gaseous fluid upwardly in said tubular member is prevented by a fluid trap formed within said cup by venous blood received therein.

26. The combined cardiotomy fluid and venous blood reservoir of claim 25 further including a support member rotationally received within said chamber, said support member defining said partition wall portion, wherein said support member further includes a support grate extending circumferentially from opposite side edges of said vertically extending partition wall portion, said support grate supporting said de-foamer element against radial collapse.

27. A combined cardiotomy fluid and venous blood reservoir apparatus comprising:
    a housing defining a chamber therein and a pair of upper inlets opening into said chamber; said housing including a bottom portion having a bottom wall, a side wall defining an upper opening, and a upper edge portion circumscribing said upper opening; a top part of said housing engaging said bottom portion at said upper edge portion to span and close said upper opening; said top part defining an upwardly opening aperture which is circular in plan view and disposed over said chamber; a turret member which is circular in plan view rotationally and sealingly received in said circular opening of said top portion, said turret member peripherally carrying one of said pair of upper inlets which is a cardiotomy fluid inlet to said apparatus; said turret member defining a centrally located aperture; and a venous blood inlet fitting sealingly and rotationally received in said centrally located aperture and defining the other of said pair of upper inlets;
    a support member rotationally received within said chamber, said support member including a vertically extending partition wall portion and a retaining portion adjacent an upper extent of said partition wall and engaging said turret member, said turret member and said support member being coupled to rotate in unison; and an annular vertically-extending liquid-permeable de-foaming element received in said chamber about said partition wall and having an open upper end into which said pair of upper inlets spill; said partition wall effectively fluidly dividing said de-foamer element horizontally into a first sector-like portion outwardly through which flows only cardiotomy fluid into a lower part of said chamber, and a second sector-like portion outwardly through which flows only venous blood;

said venous blood fitting carrying a vertically extending tubular member carrying venous blood from said venous blood inlet downwardly into said chamber, said tubular member having an opening to said chamber adjacent to a lower end thereof; and said partition wall carrying a blood-receiving cup adjacent to said lower end of said tubular member;

below said de-foamer element, said housing defining a basin portion of said chamber for receiving and combining therein of both de-foamed cardiotomy fluid and de-foamed venous blood; and an outlet leading from said basin portion for flowing de-foamed cardiotomy fluid combined with de-foamed venous blood externally of said housing.

28. The combined cardiotomy fluid and venous blood reservoir apparatus of claim 27 further including a primary cardiotomy fluid filter disposed upon said support member within said chamber and below said cardiotomy fluid inlet within said de-foamer element.

29. The combined cardiotomy fluid and venous blood reservoir apparatus of claim 28 wherein said retaining portion includes a ring member having a depending wall portion including a circumferential part of said ring member and a transverse wall portion thereof spanning a circumferential part of said ring member and forming a circular segment of said ring member, said primary cardiotomy fluid filter being configured as a bag member having an open upper end received upon said depending wall portion, and means for securing said bag member upon said ring member.

30. The combined cardiotomy fluid and venous blood reservoir apparatus of claim 29 wherein said depending wall portion includes a depending circumferential part of said ring member and a depending transverse wall portion of said ring member cooperatively forming a depending portion of said ring member which is generally D-shaped in plan view, said primary cardiotomy fluid filter being configured as a bag member having an open upper end received upon said D-shaped depending wall portion, and means for securing said bag member upon said ring member.

31. The combined cardiotomy fluid and venous blood reservoir apparatus of claim 30 wherein said means for securing said bag member upon said ring member includes a securing member circumscribing both said bag member at an upper edge portion thereof and said ring member at said D-shaped depending portion thereof.

32. The combined cardiotomy fluid and venous blood reservoir apparatus of claim 31 wherein said securing member includes a tie strap.

33. The combined cardiotomy fluid and venous blood reservoir apparatus of claim 27 wherein said de-foamer element is configured as a bag shaped member having an open upper end, said bag-shaped de-foamer element at said open upper end being received about said ring member, and means for securing said bag-shaped de-foamer element upon said ring member.

34. The combined cardiotomy fluid and venous blood reservoir apparatus of claim 33 wherein said means for securing said bag-shaped de-foamer element upon said ring member includes a securing element circumscribing both said bag-shaped de-foamer element at an upper edge portion thereof and said ring member.

35. The combined cardiotomy fluid and venous blood reservoir apparatus of claim 34 wherein said securing element includes a tie strap.

36. The combined cardiotomy fluid and venous blood reservoir apparatus of claim 35 wherein said ring member includes a pair of radially outwardly extending circumferential ridges defining an upper circumferentially continuous groove on said ring member, and said tie strap for said bag-shaped de-foamer element is received in said upper groove, a lower one of said pair of ridges cooperating with a radially outwardly extending ridge circumscribing only said D-shaped wall portion to define a lower second groove on said ring member, and said tie strap for said filter bag being received into said lower second groove.

37. The combined cardiotomy fluid and venous blood reservoir apparatus of claim 27 wherein support member further includes a support grate extending circumferentially from opposite side edges of said vertically extending partition wall portion, said support grate supporting said de-foamer element against radial collapse.

38. A combined cardiotomy fluid and venous blood reservoir for filtering and de-foaming cardiotomy fluid, and also de-foaming venous blood, and said reservoir providing filtered and de-foamed cardiotomy fluid and de-foamed venous blood together, said combined cardiotomy fluid and venous blood reservoir comprising:

a chambered housing defining a pair of upper inlets and a branched confluent flow path extending in said housing from said pair of upper inlets to a lower outlet, one of said pair of upper inlets being a cardiotomy fluid inlet while the other of said pair of inlets is a venous blood inlet;

a cardiotomy fluid filter element disposed within said housing chamber to receive cardiotomy fluid from said cardiotomy fluid inlet;

at least one de-foamer element portion disposed to receive filtered cardiotomy fluid from said filter element;

at least one de-foamer element portion disposed to receive venous blood from said venous blood inlet;

a generally vertically extending partition wall portion received within said housing chamber and substantially preventing intermixing of said cardiotomy fluid and said venous blood until both have passed though said de-foamer element portions, said cardiotomy inlet and said venous inlet positioned to deliver respective fluids on opposite sides of said partition wall portion so that a cardiotomy fluid portion is defined on one side and a venous blood portion is defined on the other, the portions being generally side-by-side;

said chambered housing defining a basin portion below said de-foamer element portion for receiving and combining therein of both de-foamed cardiotomy fluid and de-foamed venous blood; and an said outlet leading from said basin portion for flowing de-foamed cardiotomy fluid and de-foamed venous blood out of said housing.

39. The combined cardiotomy fluid and venous blood reservoir of claim 38 wherein said de-foamer element portions for separately receiving the cardiotomy fluid and venous blood together comprise a single de-foamer element, and further including a primary cardiotomy fluid filter configured as a bag member having an open upper end, said primary cardiotomy fluid filter being disposed within said chamber within said de-foamer element and below said cardiotomy fluid inlet to receive cardiotomy fluid therefrom.

40. The combined cardiotomy fluid and venous blood reservoir of claim 38 wherein said de-foamer element portions for the cardiotomy fluid and for the venous blood comprise is a single de-foamer element, and wherein said generally vertically extending partition wall portion is received within said de-foamer element and fluidly divides said de-foamer element into said cardiotomy fluid portion through which flows only cardiotomy fluid and said venous blood portion through which flows only venous blood.

41. The combined cardiotomy fluid and venous blood reservoir of claim 40 wherein said partition wall portion is at least in part offset from a central position within said chamber of said housing.

42. The combined cardiotomy fluid and venous blood reservoir of claim 40 wherein said partition wall portion defines a generally vertically extending trough allowing venous blood to flow downwardly from said venous blood inlet centrally of said chamber, said partition wall portion including a pair of offset portions one on each side of and defining said trough portion and positioning respective outer portions of said partition wall portion to fluidly divide said de-foamer element.

43. The combined cardiotomy fluid and venous blood reservoir of claim 42 further including a support member rotationally received within said chamber, said support member defining said partition wall portion and also including a retaining portion adjacent an upper extent of said partition wall member, said support member retaining and supporting said de-foamer element.

44. The combined cardiotomy fluid and venous blood reservoir of claim 43 wherein said support member also includes a blood-receiving cup adjacent to and carried by a lower extent of said partition wall portion, said reservoir including a tubular member descending in said trough of said partition wall member from said venous blood inlet and having a lower end with an outlet disposed within said cup to prevent reflux of air up said tubular member when said cup is filled with venous blood.

45. A combined cardiotomy fluid and venous blood reservoir comprising:

a housing defining a chamber therein and a pair of upper inlets opening into said chamber, one of said pair of upper inlets being a cardiotomy fluid inlet while the other of said pair of inlets is a venous blood inlet;

an annular vertically-extending liquid-permeable de-foamer element received in said chamber and having an upper end into which said pair of upper inlets spill;

a generally vertically extending partition wall portion received within said de-foamer element between said pair of upper inlets and effectively fluidly dividing said de-foamer element horizontally into a first portion through which flows only cardiotomy fluid, and a second portion through which flows only venous blood;

a support member rotationally received within said chamber, said support member defining said partition wall portion and also including a retaining portion adjacent an upper extent of said partition wall portion;

a primary cardiotomy fluid filter disposed upon said retaining portion of said support member within said chamber and below said cardiotomy fluid inlet within said de-foamer element;

a basin portion of said housing chamber defined below said de-foamer element for receiving both de-foamed cardiotomy fluid and de-foamed venous blood from said second de-foamer element portion; and an outlet leading from said basin portion for flowing de-foamed cardiotomy fluid and de-foamed venous blood out of said housing.

46. The combined cardiotomy fluid and venous blood reservoir of claim 45 wherein said retaining portion includes a depending wall portion including a circumferentially extending part of said retaining portion and a transverse wall portion thereof forming a segment of said retaining portion, said primary cardiotomy fluid filter being configured as a bag member having an open upper end, and said bag member at said open upper end being received upon said depending wall portion, and means for securing said bag member upon said retaining portion.

47. The combined cardiotomy fluid and venous blood reservoir of claim 46 wherein said retaining portion includes a circular ring portion and said depending wall portion cooperates with said ring portion to cooperatively define a portion thereof which is generally D-shaped in plan view.

48. The combined cardiotomy fluid and venous blood reservoir of claim 46 wherein said means for securing said primary cardiotomy fluid filter bag member upon said retaining portion includes a securing member circumscribing both said bag member at an upper edge portion thereof and a part of said retaining portion at said D-shaped depending wall portion thereof.

49. The combined cardiotomy fluid and venous blood reservoir of claim 48 wherein said securing member includes a tie strap.

50. The combined cardiotomy fluid and venous blood reservoir of claim 47 wherein said de-foamer element is also configured as a bag-shaped member having a circular open upper end, said bag-shaped de-foamer element at said circular open upper end being received about said ring portion, and means for securing said bag-shaped de-foamer element upon said ring portion.

51. The combined cardiotomy fluid and venous blood reservoir apparatus of claim 50 wherein said means for securing said bag-shaped de-foamer element upon said ring portion includes an elongate securing member circumscribing both said bag-shaped de-foamer element at an upper edge portion thereof and said ring portion.

52. The combined cardiotomy fluid and venous blood reservoir apparatus of claim 51 wherein said elongate securing member includes a tie strap.

53. The combined cardiotomy fluid and venous blood reservoir apparatus of claim 48 wherein said ring portion includes a pair of radially outwardly extending circumferential ridges defining an upper circumferentially continuous groove on said ring portion, and said tie strap for said bag-shaped de-foamer element is received in said upper groove, a lower one of said pair of ridges cooperating with a radially outwardly extending ridge circumscribing only said D-shaped wall portion to define a lower second groove on said ring portion, and said tie strap for said primary cardiotomy fluid filter bag being received into said lower second groove.

54. The combined cardiotomy fluid and venous blood reservoir of claim 45 wherein said support member further includes a support grate extending circumferentially from opposite side edges of said vertically extending partition wall portion, said support grate supporting said de-foamer element against radial collapse.

55. A combined cardiotomy fluid and venous blood reservoir comprising:

a housing defining a chamber therein and a pair of upper inlets opening into said chamber, one of said pair of upper inlets being a cardiotomy fluid inlet while the other of said pair of inlets is a venous blood inlet, said housing including a top part defining an upwardly opening aperture which is circular in plan view and which is disposed over said chamber;

a turret member which is circular in plan view being rotationally and sealingly received in said circular opening of said top part and defining said cardiotomy fluid inlet, said turret member defining a centrally located aperture;

a venous blood inlet fitting sealingly and rotationally received in said centrally located aperture and defining said venous blood inlet;

an annular vertically-extending liquid-permeable de-foamer element received in said chamber and having an upper end into which said pair of upper inlets spill;

a generally vertically extending partition wall portion received within said de-foamer element between said pair of upper inlets and effectively fluidly dividing said de-foamer element horizontally into a first portion through which flows only cardiotomy fluid, and a second portion through which flows only venous blood;

a basin portion of said housing chamber defined below said de-foamer element for receiving both de-foamed cardiotomy fluid and de-foamed venous blood from said second de-foamer element portion; and an outlet leading from said basin portion for flowing de-foamed cardiotomy fluid and de-foamed venous blood out of said housing.

56. The combined cardiotomy fluid and venous blood reservoir of claim 55 further including a support member rotationally received within said chamber, said support member defining said partition wall portion, wherein said turret member and said support member define cooperating means for drivingly coupling said turret with said support member so that manual rotation of said turret member rotates said support member in unison therewith.

57. The combined cardiotomy fluid and venous blood reservoir of claim 55 wherein said venous blood fitting carries a vertically extending tubular member carrying venous blood from said venous blood inlet downwardly into said chamber, said tubular member having an opening to said chamber adjacent to a lower end thereof, and said partition wall carrying a blood-receiving cup adjacent to said lower end of said tubular member and receiving said lower end of said tubular member.

58. The combined cardiotomy fluid and venous blood reservoir of claim 57 wherein said blood-receiving cup supports a lower portion of said tubular member.

59. The combined cardiotomy fluid and venous blood reservoir of claim 58 wherein said blood-receiving cup includes a radially extending flange having a horizontally extending surface portion engageable by said lower end of said tubular member to support the latter.

60. The combined cardiotomy fluid and venous blood reservoir of claim 59 wherein said radially extending flange of said blood-receiving cup includes a step defining said a horizontally extending surface portion and also providing a vertically extending surface portion engageable by said tubular member to constrain said tubular member within said cup.

61. The combined cardiotomy fluid and venous blood reservoir of claim 57 wherein said blood-receiving cup includes a peripheral wall portion cooperating with said partition wall and having an upper edge at a higher elevation than said opening of said tubular member.

62. The combined cardiotomy fluid and venous blood reservoir of claim 57 wherein said blood-receiving cup also includes at least two convergent flanges extending toward but short of intersection with one another and being stepped to each define both a horizontally extending support edge confronting said lower end of said tubular member and a vertically extending locating edge engageable with an outer surface of said tubular member to position the latter within said blood-receiving cup.

63. A combined cardiotomy fluid and venous blood reservoir for filtering and de-foaming cardiotomy fluid, and also de-foaming venous blood, and said reservoir providing filtered and de-foamed cardiotomy fluid and de-foamed venous blood together, said combined cardiotomy fluid and venous blood reservoir comprising:

a chambered housing defining a pair of upper inlets and a branched confluent flow path extending in said housing from said pair of upper inlets to a lower outlet, one of said pair of upper inlets being a cardiotomy fluid inlet while the other of said pair of inlets is a venous blood inlet;

a cardiotomy fluid filter element disposed within said housing chamber to receive cardiotomy fluid from said cardiotomy fluid inlet;

a de-foamer element including at least one portion disposed to receive filtered cardiotomy fluid from said filter element and at least one portion disposed to receive venous blood from venous blood inlet;

a partition wall portion received within said housing chamber and substantially preventing intermixing of said cardiotomy fluid and said venous blood until both have passed though said de-foamer element portions, wherein said partition wall portion is received within said chamber of said housing and within said de-foamer element and fluidly divides said de-foamer element into a cardiotomy fluid portion through which flows only cardiotomy fluid and a venous blood portion through which flows only venous blood;

a generally vertically extending trough defined by said partition wall portion allowing venous blood to flow downwardly from said venous blood inlet centrally of said chamber, said partition wall portion including a pair of offset portions one on each side of and defining said trough portion and positioning respective outer portions of said partition wall portion to fluidly divide said de-foamer element;

a support member rotationally received within said chamber, said support member defining said partition wall portion and also including a retaining portion adjacent an upper extent of said partition wall member, said support member retaining and supporting said de-foamer element;

said chambered housing defining a basin portion below said de-foamer element for receiving and combining therein of both de-foamed cardiotomy fluid and de-foamed venous blood; and an said outlet leading from said basin portion for flowing de-foamed cardiotomy fluid and de-foamed venous blood out of said housing.

64. The combined cardiotomy fluid and venous blood reservoir of claim 63 wherein said support member also includes a blood-receiving cup adjacent to and carried by a lower extent of said partition wall portion, said reservoir including a tubular member descending in said trough of said partition wall member from said venous blood inlet and having a lower end with an outlet disposed within said cup to prevent reflux of air up said tubular member when said cup is filled with venous blood.

65. A combined cardiotomy fluid and venous blood reservoir comprising:

a housing defining a chamber therein and a pair of upper inlets opening into said chamber, one of said pair of upper inlets being a cardiotomy fluid inlet while the other of said pair of inlets is a venous blood inlet;

said housing including a top part defining an upwardly opening aperture which is circular in plan view and which is disposed over said chamber;

a turret member which is circular in plan view being rotationally and sealingly received in said circular opening of said top part and defining the one of said pair of inlets which is said cardiotomy fluid inlet; said turret member defining a centrally located aperture;

a venous blood inlet fitting sealingly and rotationally received in said centrally located aperture and defining the other of said pair of upper inlets which is said venous blood inlet, wherein said cardiotomy fluid and venous blood inlets are independently rotatable relative to said housing and to each other;

at least one de-foamer element portion disposed to receive cardiotomy fluid from said cardiotomy fluid inlet;

at least one de-foamer element portion disposed to receive venous blood from said venous blood inlet;

a basin portion of said housing chamber defined below said inlets for receiving both de-foamed cardiotomy fluid and de-foamed venous blood from said de-foamer element portions; and an outlet leading from said basin portion for flowing de-foamed cardiotomy fluid and de-foamed venous blood out of said housing.

66. The combined cardiotomy fluid and venous blood reservoir of claim 65, wherein said de-foamer element portions for receiving the cardiotomy fluid and venous blood together comprise a single bag-type de-foamer element disposed within said chamber and having an open upper end positioned below both said inlets, and further including a primary cardiotomy fluid filter configured as a bag member having an open upper end, said primary cardiotomy fluid filter being disposed within said de-foamer element and below said cardiotomy fluid inlet to receive cardiotomy fluid therefrom, wherein filtered cardiotomy fluid and venous blood pass through said defoamer element and mix in said basin portion before flowing through said outlet.

67. The combined cardiotomy fluid and venous blood reservoir of claim 65, wherein said de-foamer element portions for receiving the cardiotomy fluid and venous blood together comprise a single bag-type de-foamer element disposed within said chamber and having an open upper end positioned below both said inlets, and further including a generally vertically extending partition wall portion received within said de-foamer element between said pair of upper inlets and effectively fluidly dividing said de-foamer element horizontally into said de-foamer element portion disposed to receive cardiotomy fluid from said cardiotomy fluid inlet, and said de-foamer element portion disposed to receive venous blood from said venous blood inlet.

68. The combined cardiotomy fluid and venous blood reservoir of claim 67 further including a blood-receiving cup adjacent to and carried by a lower extent of said partition wall portion, a generally vertically extending trough defined by said partition wall portion allowing venous blood to flow downwardly from said venous blood inlet centrally of said chamber, said reservoir including a tubular member descending in said trough of said partition wall member from said venous blood inlet and having a lower end with an outlet disposed within said cup to prevent reflux of air up said tubular member when said cup is filled with venous blood.

* * * * *